US005976460A

United States Patent [19]

Bourson et al.

[11] Patent Number: 5,976,460

[45] **Date of Patent: *Nov. 2, 1999**

[54] USE OF A DEODORIZER BASED ON UNDECYLENIC ACID OR ON DERIVATIVES OF THE SAID ACID TO DEODORIZE PAPERS, CARDBOARDS AND NONWOVENS

[75] Inventors: Lucien Bourson, Bois-Colombes; Henri-Jean Caupin, Versailles, both of France

[73] Assignee: Elf Atochem S.A., France

[ * ] Notice: This patent issued on a continued prosecution application filed under 37 CFR 1.53(d), and is subject to the twenty year patent term provisions of 35 U.S.C. 154(a)(2).

[21] Appl. No.: 08/772,517

[22] Filed: Dec. 24, 1996

[30] Foreign Application Priority Data

Dec. 26, 1995 [FR] France .................................. 95 15477

[51] Int. Cl.$^{6}$ ....................................................... A61L 9/01

[52] U.S. Cl. ............................ 422/5; 424/76.1; 424/76.2

[58] Field of Search .................................. 422/5, 120, 4; 210/749, 916; 424/76.1, 76.2

[56] References Cited

U.S. PATENT DOCUMENTS

| | | | |
|---|---|---|---|
| 3,882,868 | 5/1975 | Tundermann . | |
| 3,899,616 | 8/1975 | Simonelli . | |
| 4,898,727 | 2/1990 | Osada et al. | 424/76.1 |
| 4,909,986 | 3/1990 | Kobayashi et al. | 422/4 |
| 4,959,207 | 9/1990 | Ueda et al. | 424/76.1 |
| 5,182,103 | 1/1993 | Nakane et al. | 424/78.03 |
| 5,275,783 | 1/1994 | Menassa et al. | 422/5 |
| 5,338,511 | 8/1994 | Menassa et al. | 422/5 |
| 5,439,641 | 8/1995 | Caupin et al. | 422/5 |
| 5,539,034 | 7/1996 | Caupin et al. . | |

FOREIGN PATENT DOCUMENTS

| | | |
|---|---|---|
| 434522 | 6/1991 | European Pat. Off. . |
| 434523 | 6/1991 | European Pat. Off. . |
| 434524 | 6/1991 | European Pat. Off. . |
| 596772 | 5/1994 | European Pat. Off. . |
| 2655856 | 6/1991 | France . |
| 2655857 | 6/1991 | France . |
| 2694197 | 2/1994 | France . |
| 1792467 | 11/1971 | Germany . |
| 2263509 | 7/1974 | Germany . |
| 2655819 | 6/1991 | Germany . |
| 2269587 | 2/1994 | United Kingdom . |

OTHER PUBLICATIONS

French Search Report dated Sep. 11, 1996.

*Primary Examiner*—Krisanne Thornton
*Attorney, Agent, or Firm*—Bell, Boyd & Lloyd

[57] ABSTRACT

The invention relates to the use of a deodorizer including undecylenic acid or a salt or an alkyl or polyoxyalkylenic ester or undecylenic acid to deodorize papers, cardboards and nonwovens. The invention also relates to papers, cardboards and nonwovens containing the above mentioned deodorizer.

11 Claims, No Drawings

USE OF A DEODORIZER BASED ON UNDECYLENIC ACID OR ON DERIVATIVES OF THE SAID ACID TO DEODORIZE PAPERS, CARDBOARDS AND NONWOVENS

FIELD OF THE INVENTION

The invention relates to the use of a deodorizer comprising undecylenic acid or a salt or an ester of undecylenic acid to deodorize papers, cardboards and nonwovens.

BACKGROUND OF THE INVENTION

Compositions based on undecylenic acid ester which are capable of attenuating certain undesirable odors are already known in the field of deodorization.

Thus, DE-A-2,263,509 proposes a complex deodorizing composition comprising a ($C_1$–$C_4$) alkyl ester of undecylenic acid to prevent the development of the microorganisms responsible for body odor in man.

DE-A-1,792,467 describes a composition intended to repel wild game which damage crops, based on undecylenic acid optionally combined, inter alia, with unsaturated fatty acid esters such as methyl undecylenate.

It is also known to use compositions based on undecylenic acid ester to deodorize the sludges of purification plants, liquid manures, animal feeds and paper industry effluents (see FR 2,655,856, FR 2,655,857, FR 2,655,819 and FR 2,694,197).

As regards supports of cellulosic nature, there is a great need to deodorize them either because they have a pronounced specific odor or because they are intended to come into contact with unpleasant-smelling products.

The need for deodorization in the sense defined above is evident in the case of packaging cardboards and papers before or after printing, the intrinsic odors of which is disagreeable. This need is also seen when it is desired to use papers or nonwovens as deodorizer support, in particular to filter gases (air conditioning, industrial environment), liquids or particles (vacuum cleaner bags), to collect human excrement (nappies) or animal excrement (litter) or alternatively to act in a confined atmosphere (air-freshener diffusers).

DESCRIPTION OF THE INVENTION

It has now been found that compositions based on undecylenic acid or on a salt or ester of undecylenic acid prove to be particularly effective for deodorizing papers, cardboards and nonwovens.

More precisely, the invention relates to the use of an odor-absorbing substance, characterized in that the said substance comprises undecylenic acid or a salt or an alkyl or polyoxyalkylenic ester of undecylenic acid.

Among these products, the invention relates most particularly to metal salts and alkyl esters containing from 1 to 12 carbon atoms and polyoxyethylene, polyoxypropylene and poly(oxyethylene) (oxypropylene) esters of the said undecylenic acid. The invention relates more precisely to the Na, K, Zn, Ca and Cu, methyl, ethyl, propyl, hexyl and decyl undecylenates as well as to polyoxyalkylenic esters containing from 2 to 20 oxyalkylene units.

The absorbent substance used in accordance with the invention may consist of one of the above-mentioned products alone or a mixture of the said products, it being possible for this or these products themselves to be used as they are or in solution, suspension or emulsion form or alternatively in a form adsorbed onto a support, in particular a solid support such as clay, zeolites or diatomaceous earths.

The undecylenic acid and the undecylenic salts or esters are generally effective at low dose, for example from about 0.05 to 10% by weight, and preferably 0.05 to 3, relative to the support to be treated.

It is naturally possible to form compositions comprising undecylenic acid or the above-mentioned undecylenic salt(s) or ester(s) and additives intended, in particular to improve the mechanical properties, the appearance, the resistance to fats, to water penetration, the surface state etc.

Compositions based on the above-mentioned compounds are generally used on any type of support comprising cellulose fibers, such as papers, cardboards and nonwovens. It is most particularly recommended to deodorize special papers. Illustrations of these papers which may be mentioned are cigarette papers, papers for filtering (coffee, vacuum cleaner or for industrial use), for condensers, for joints, parchment or grease-proof papers, drawing papers, wall papers, silicone-coating papers or self-adhesive coating papers, security papers, geographic papers, blotting papers, papers for abrasives, self-copying papers, papers for wiping, for medical use and for packaging metal components or animal feeds.

EXAMPLES

The examples which follow allow the invention to be illustrated.

Example 1

A non-coated paper for offset printing, with a G.S.M. of 70 g/m$^2$, is prepared conventionally from the following composition (in % by weight):

| | |
|---|---|
| Bleached softwood kraft pulp (KBR) | 30 |
| Bleached hardwood kraft pulp (KBF) | 70 |
| $CaCO_3$ | 15 (relative to the fibres) |
| AKD | 1 |
| Cationic starch | 0.4 (relative to the composition) |
| PAA | 200 g/t of paper |
| Methyl undecylenate | 0.01 to 2 |

Oxidized starch is deposited, using a size press, onto both faces of the paper thus obtained (3 g/m$^2$/side).

The paper is printed using an offset ink (tack grade No. 5; Lorieux).

The extent to which the odor of the printed paper can be detected is evaluated by a group of six individuals who give a rating ranging from 0 to 6, the extreme values 0 to 6 respectively meaning: absence of ink odor and original odor of the ink.

The results are presented below by comparison with a control paper containing no methyl undecylenate.

| Methyl undecylenate (% by weight) | 0.01 | 0.05 | 0.5 | 2 | Control |
|---|---|---|---|---|---|
| Rating | 6 | 4 | 2 | 1 | 6 |

Example 2

An aqueous emulsion containing 10% by weight of methyl undecylenate (Maskod MNS 01-10; EC11) is deposited using a size press onto a non-coated paper (70 m$^2$/g)

The paper is printed using an offset ink (tack grade No. 5; Lorieux). The extent to which the odor of the printed paper can be detected is measured under the conditions of Example 1 by comparison with a control paper free of methyl undecylenate.

| Methyl undecylenate (% by weight) | 0.01 | 0.05 | 0.5 | 2 | Control |
|---|---|---|---|---|---|
| Rating | 5 | 3 | 1 | 0 | 6 |

Example 3

A paper intended for packaging dry animal feed (granules) is prepared from a bleached chemical pulp (G.S.M. 80 g/m$^2$) and is adhesively bonded in neutral medium using alkylketene dimers (Cobb 60=18 g/m$^2$). The paper obtained is made impermeable to fats by a treatment with Foraperle 321 (Elf Atochem S.A.) and impregnated on a size press with an aqueous emulsion containing 10% by weight of methyl undecylenate (Maskod MNS 01-10; EC11) and 0.2% by weight of carboxymethylcellulose.

The paper thus obtained contains 3 g/m$^2$ of methyl undecylenate.

Using this paper, 100 g of granules are packaged and the package is placed in a jar which is placed in an oven at 50° C. for 24 hours.

No odor is detected on opening the jar, whereas a control jar containing granules packaged in the same paper free of methyl undecylenate has a very strong odor of feed.

The granules packaged in the treated paper are entirely accepted by the animals.

Example 4

A nonwoven fabric (60 g/m$^2$) is prepared from a fibrous composition containing 50% by weight of chemical pulp and 50% by weight of polypropylene fibers.

The fabric obtained is impregnated on a size press with an aqueous emulsion containing 10% by weight of methyl undecylenate (Maskod MNS 01-10; EC11) and 0.1% by weight of carboxymethylcellulose. This impregnated fabric contains 1 g/m$^2$ of methyl undecylenate.

The fabric is placed in the walking shoes of 6 users. After 10 days of use, no odor is detected.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Method for deodorizing paper, cardboard, and nonwovens comprising adding to the paper, cardboard and nonwovens during preparation thereof and in solution, suspension or emulsion form, an effective deodorizing amount of at least one composition of undecylenic acid or salt or a $C_1$ to $C_{12}$ alkyl or polyoxyalkylanic ester containing from 2 to 20 oxyalkylene units of undecylenic acid to deodorize the paper, cardboard and nonwovens, said at least one composition being added when the paper, cardboard or nonwovens are in a pulp state or at a sizing press.

2. Method according to claim 1, wherein the salt is a metal salt.

3. Method according to claim 2, wherein the salt is Na, K, Zn, Ca or Cu undecylenate.

4. Method according to claim 1, wherein the ester is selected from polyoxyethylene, polyoxypropylene and poly (oxyethylene) (oxypropylene) esters of undecylenic acid.

5. Paper containing a deodorizer according to claim 1.

6. Cardboard containing a deodorizer according to claim 1.

7. Nonwoven articles containing a deodorizer according to claim 1.

8. Method according to claim 1, wherein the effective amount is 0.05 to 10% by weight.

9. Method according to claim 8, wherein the effective amount is 0.05 to 3% by weight.

10. Method for deodorizing paper, cardboard and/or nonwovens comprising adding to the paper, cardboard or nonwovens during manufacture thereof an effective amount of at least one composition selected from the group consisting of undecylenic acids, salts, alkyls, polyoxyalkylenic esters of undecylenic acid and mixtures thereof for deodorizing the articles, said at least one composition being added in solution, suspension or emulsion form when the paper, cardboard or nonwovens are in a pulp state or at a sizing press.

11. Method according to claim 10, wherein the ester is selected from alkyl esters containing from 1 to 12 carbon atoms and polyoxyethylene, polyoxypropylene and poly (oxyethylene) (oxypropylene) esters of undecylenic acid.

* * * * *